United States Patent
Al Shahri et al.

(10) Patent No.: US 11,719,683 B2
(45) Date of Patent: Aug. 8, 2023

(54) AUTOMATED REAL-TIME WATER CUT TESTING AND MULTIPHASE FLOWMETER CALIBRATION ADVISORY

(71) Applicant: Saudi Arabian Oil Company, Dhahran (SA)

(72) Inventors: Ali M. Al Shahri, Dhahran (SA); Anas A. Al Shuaibi, Dammam (SA); Mohammed Sami Kanfar, Dammam (SA); Kalid Saad Dosary, Al-Khobar (SA); Abdulaziz A. Alsaleh, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 291 days.

(21) Appl. No.: 17/215,591

(22) Filed: Mar. 29, 2021

(65) Prior Publication Data
US 2021/0302405 A1    Sep. 30, 2021

Related U.S. Application Data

(60) Provisional application No. 63/002,469, filed on Mar. 31, 2020.

(51) Int. Cl.
*G01N 33/28*    (2006.01)
*E21B 47/07*    (2012.01)
*E21B 47/06*    (2012.01)

(52) U.S. Cl.
CPC ......... *G01N 33/2847* (2013.01); *E21B 47/06* (2013.01); *E21B 47/07* (2020.05);
(Continued)

(58) Field of Classification Search
CPC ............ G01N 33/2847; G01N 33/2823; E21B 47/07; E21B 47/06; E21B 2200/20; E21B 2200/22
See application file for complete search history.

(56) References Cited

U.S. PATENT DOCUMENTS

4,726,219 A    2/1988    Pearson et al.
4,856,344 A *  8/1989    Hunt .................. G01F 1/88
                                                73/861.63
(Continued)

FOREIGN PATENT DOCUMENTS

WO    2019112597 A1    6/2019

OTHER PUBLICATIONS

Kevin Beck, "How to Calculate Dynamic Pressure", https://sciencing.com/calculate-dynamic-pressure-7895595.html, updated Dec. 15, 2020 (Year: 2020).*

(Continued)

*Primary Examiner* — Regis J Betsch
(74) *Attorney, Agent, or Firm* — Dinsmore & Shohl LLP

(57) ABSTRACT

Systems and methods for generating pressure data from at least two pressure sensors, storing one or more parameters indicative of water cut in a neural network model, receiving pressure data from at least the two pressure sensors respectively indicative of the pressure at two points of a well bore, determining a pressure drop between the two points, generating an input water cut estimate, estimating a dynamic pressure loss to initiate an iterative process, estimating a potential energy loss, inverse modeling a water cut estimate, comparing the water cut estimate to the input water cut estimate to generate a water cut Δ, utilizing the water cut estimate as the input water cut estimate for the iterative process when the water cut Δ exceeds a threshold, and continuing the iterative process until the water cut Δ is below the threshold.

18 Claims, 5 Drawing Sheets

(52) U.S. Cl.
CPC ...... *G01N 33/2823* (2013.01); *E21B 2200/20* (2020.05); *E21B 2200/22* (2020.05)

(56) References Cited

U.S. PATENT DOCUMENTS

| | | | |
|---|---|---|---|
| 5,597,961 A * | 1/1997 | Marrelli | G01F 1/363 |
| | | | 73/861.04 |
| 8,170,801 B2 | 5/2012 | Foot et al. | |
| 8,527,219 B2 | 9/2013 | Camilleri | |
| 9,671,524 B2 | 6/2017 | Abitrabi et al. | |
| 9,803,470 B2 | 10/2017 | Mashetty et al. | |
| 10,072,485 B2 | 9/2018 | Machado et al. | |
| 10,301,923 B2 | 5/2019 | Andresen et al. | |
| 2002/0139197 A1* | 10/2002 | Salamitou | G01F 1/74 |
| | | | 73/861.04 |
| 2010/0305882 A1 | 12/2010 | Gysling | |
| 2012/0168153 A1* | 7/2012 | Joseph | E21B 47/10 |
| | | | 166/250.03 |
| 2013/0081460 A1* | 4/2013 | Xiao | E21B 47/10 |
| | | | 73/152.29 |
| 2013/0166216 A1 | 6/2013 | Foot et al. | |
| 2017/0058664 A1* | 3/2017 | Xiao | E21B 47/06 |
| 2018/0245463 A1 | 8/2018 | Shako et al. | |
| 2018/0306693 A1 | 10/2018 | Nazari et al. | |
| 2020/0150620 A1 | 5/2020 | Gray et al. | |
| 2020/0150634 A1 | 5/2020 | Gray et al. | |

OTHER PUBLICATIONS

Al Enezi et al., "Forecasting and Monitoring Water Cut Utilizing ESP Pump Discharge Pressures and Fluid PVT Analysis", Society of Petroleum Engineers, SPE 160886, Apr. 8-11, 2012.

Camilleri et al., "Obtaining Real-Time Flow Rate, Water Cut, and Reservoir Diagnostics from ESP Gauge Data", Society of Petroleum Engineers, SPE 145542, Sep. 6-8, 2011.

International Search Report and Written Opinion dated Jul. 1, 2021 pertaining to International application No. PCT/US2021/024632 filed Mar. 29, 2021, 16 pages.

* cited by examiner

AUTOMATED REAL-TIME WATER CUT TESTING AND MULTIPHASE FLOWMETER CALIBRATION ADVISORY

CROSS-REFERENCE TO RELATED APPLICATIONS

This application claims the benefit of U.S. Provisional Application Ser. No. 63/002,469, filed Mar. 31, 2020, entitled "AUTOMATED REAL-TIME WATER CUT TESTING AND MULTIPHASE FLOWMETER CALIBRATION ADVISORY," the entirety of which is incorporated by reference herein.

TECHNICAL FIELD

The present disclosure relates to automated real-time water cut testing and multiphase flowmeter calibration advisory and, in particular, systems and methods for automated real-time water cut testing and multiphase flowmeter calibration advisory based on real-time pressure.

BACKGROUND

A water cut flowmeter measures water content (cut) of crude oil and hydrocarbons as they flow from a well and through a pipeline. Water cut measurements can be made by providing one multi-phase flowmeter per drill site or platform. Oil from the wells is then flowed to the multiphase flowmeter from each well to measure water cut, and each measurement typically takes around a day to measure to allow the flow to stabilize. However, the water cut measurements through such measurement systems may not be continuous but rather intermittent. For example, wells may be tested approximately one time per month based on how many wells are connected to a single flowmeter. Further, the flowmeter itself may be subject to drifting and be off calibration when taking measurements, which may lead to misleading results. Alternatively, placing a multi-phase flowmeter at each well would be a costly option. A need exists for alternative systems and methods to accurately estimate water cut.

BRIEF SUMMARY

According to the subject matter of the present disclosure, an intelligent water cut estimation system may include at least two pressure sensors, a neural network model, and a data processor. The at least two pressure sensors are configured to generate pressure data respectively associated with two points of a well bore. The neural network model may include one or more parameters indicative of water cut associated with a well bore. The data processor is communicatively coupled to the at least two pressure sensors and the neural network model and is operable to receive pressure data from the at least two pressure sensors respectively indicative of the pressure at each of the two points of the well bore, determine a pressure drop between the two points based on the received pressure data from the at least two pressure sensors, generate an input water cut estimate, and estimate a dynamic pressure loss based on the pressure drop, the one or more parameters of the neural network model, and the input water cut estimate to initiate an iterative process. The data processor is further operable to estimate a potential energy loss based on the dynamic pressure loss and the pressure drop, inverse model a water cut estimate based on the potential energy loss, compare the water cut estimate to the input water cut estimate to generate a water cut $\Delta$, utilize the water cut estimate as the input water cut estimate for the iterative process when the water cut $\Delta$ exceeds a threshold, and continue the iterative process until the water cut $\Delta$ is below the threshold.

In accordance with one embodiment of the present disclosure, an intelligent water cut estimation system may include at least two pressure sensors, at least two temperature sensors, a neural network model, and a data processor. The at least two pressure sensors are configured to generate pressure data respectively associated with two points of a well bore. The at least two temperature sensors are configured to generate temperature data respectively associated with two points of a well bore. The neural network model may include one or more parameters indicative of water cut associated with a well bore. The data processor is communicatively coupled to the at least two pressure sensors and the neural network model and is operable to receive pressure data from the at least two pressure sensors respectively indicative of the pressure at each of the two points of the well bore, receive temperature data from the at least two temperature sensors respectively indicative of the temperature at each of the two points of the well bore, determine a pressure drop between the two points based on the received pressure data from the at least two pressure sensors, generate an input water cut estimate based on at least the one or more parameters of the neural network model and the received temperature data, and estimate a dynamic pressure loss based on the pressure drop, the one or more parameters of the neural network model, and the input water cut estimate to initiate an iterative process. The data processor is further operable to estimate a potential energy loss based on the dynamic pressure loss and the pressure drop, inverse model a water cut estimate based on the potential energy loss, compare the water cut estimate to the input water cut estimate to generate a water cut $\Delta$, utilize the water cut estimate as the input water cut estimate for the iterative process when the water cut $\Delta$ exceeds a threshold, and continue the iterative process until the water cut $\Delta$ is below the threshold.

In accordance with another embodiment of the present disclosure, an intelligent water cut estimation method may include generating pressure data from at least two pressure sensors respectively associated with two points of a well bore, storing one or more parameters indicative of water cut associated with a well bore in a neural network model, receiving pressure data, by a data processor, from at least the two pressure sensors respectively indicative of the pressure at two points of the well bore, determining a pressure drop between the two points based on the received pressure data from the at least two pressure sensors, generating an input water cut estimate, and estimating a dynamic pressure loss based on the pressure drop, the one or more parameters of a neural network model, and the input water cut estimate to initiate an iterative process. The method further may include estimating a potential energy loss based on the dynamic pressure loss and the pressure drop, inverse modeling a water cut estimate based on the potential energy loss, comparing the water cut estimate to the input water cut estimate to generate a water cut $\Delta$, utilizing the water cut estimate as the input water cut estimate for the iterative process when the water cut $\Delta$ exceeds a threshold, and continuing the iterative process until the water cut $\Delta$ is below the threshold.

Although the concepts of the present disclosure are described herein with primary reference to systems and methods for intelligent water cut estimation, it is contemplated that the concepts will enjoy applicability to any fluid transfer system that may be subject to periodic water cut measurement. For example, and not by way of limitation, it is contemplated that the concepts of the present disclosure will enjoy applicability to fluid extraction sites.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In embodiments described herein, an intelligent water cut measurement module is described to implement systems and methods to generate an automated water cut estimation determination. Embodiments of the present disclosure are directed to an intelligent water cut measurement system, as described in greater detail further below, to automate real-time water cut testing and multiphase flowmeter calibration advisory based on real-time pressure and temperature.

Embodiments described herein are directed to systems, methods, and computer programs for estimating water cut (WC) of wells in real-time from indirect measurements such as real-time pressure and temperature. Such real-time measurements provide resources to benchmark multi-phase flowmeters, instantly identify malfunctioning flowmeters, and/or optimize flowmeter calibration frequencies and flowmeter calibration scheduling. Furthermore, the intelligent water cut estimations described herein permit an interpolation between the often sparse water cut measurements and an automatic determination of production allocation per well in real-time. The intelligent water cut estimations described herein can be implemented in many fields as being based on data from pressure and temperature sensors and an estimated liquid gross rate, as described in greater detail below. Liquid gross rate can be reliably measured through flowmeters (e.g. Venturi based flowmeters, Coriolis based flowmeters, and other suitable flowmeters as known to one of ordinary skill of the art or yet-to-be-contemplated) or estimated through artificially intelligent systems. Furthermore, pressure and temperature can also be reliably measured at surface through wellhead sensors and at subsurface through permanent downhole gauges or Electrical Submersible Pump (ESP) sensors.

Figure 1:
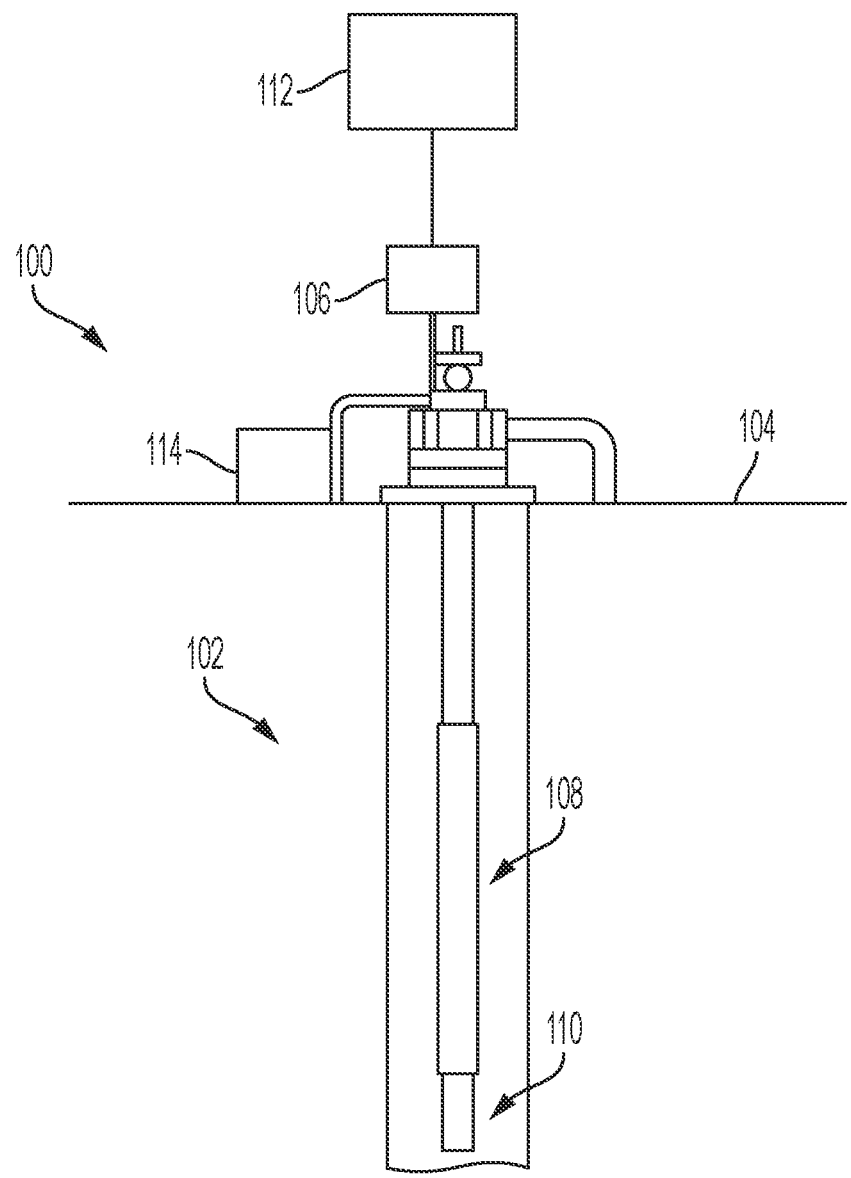
FIG. 1 schematically illustrates an intelligent water cut measurement solution utilizing a data analytics module, according to one or more embodiments shown and described herein.

Referring to FIG. 1, for example, an intelligent water cut measurement solution 100 utilizes at least a well comprising a well bore 102 to transmit temperature and pressure data of the well via one or more sensors to a data analytics module 112. The well bore 102 may house an ESP 108 coupled to the one or more sensors. The one or more sensors may include one or more temperature and/or pressure sensors 110 coupled to the ESP 108. The one or more sensors may further include a temperature and/or pressure sensor 106 on a ground surface 104 to transmit data to the data analytics module 112. The one or more sensors may further include a flowmeter 114 to transmit data to the data analytics model 112.

The intelligent water cut estimation system 300 may include at least two pressure sensors 106, 110, a neural network model associated with a machine learning module 316, and a data processor 304 as set forth in FIG. 4, described in greater detail further below. The at least two pressure sensors may be configured to generate pressure data respectively associated with two points of the well bore 102. The neural network model may include one or more parameters indicative of water cut associated with the well bore 102. The data processor is communicatively coupled to the at least two pressure sensors and the neural network model and is operable to perform the control schemes of processes 200A, 200B of FIGS. 2A-2B as described in greater detail further below. In further embodiments, the intelligent water cut estimation system may include at least two temperature sensors 106, 110 configured to generate temperature data respectively associated with two points of the well bore 102 and communicatively coupled to the data processor 304.

In embodiments, the data processor 304 is operable to receive pressure data from the at least two pressure sensors 106, 110 respectively indicative of the pressure at each of the two points of the well bore 102 and determine a pressure drop between the two points based on the received pressure data from the at least two pressure sensors 106, 110. The data processor 304 may further be operable to receive temperature data from the at least two temperature sensors 106, 110 respectively indicative of the temperature at each of the two points of the well bore 102.

As a non-limiting example, and referring to FIG. 2A, a process 200A for use of the intelligent water cut measurement solution 100 of FIG. 1 is depicted and may be implemented by an intelligent water cut measurement system 300 as described in greater detail below with respect to FIG. 4. In block 202 of the process 200A of FIG. 2A, flow parameters are measured including temperature and pressure drop across two points, such as in and associated with the well bore 102 of FIG. 1. The intelligent water cut estimation described herein is based on the fact that pressure drop from one point to another is a function of many factors but most importantly of water cut. Hence, if all other factors are to be isolated, water cut can be determined from the pressure drop across two points. The learning of water cut impact on pressure drop between two gauges may be accomplished via machine learning of large scrutinized datasets.

Figure 2A:
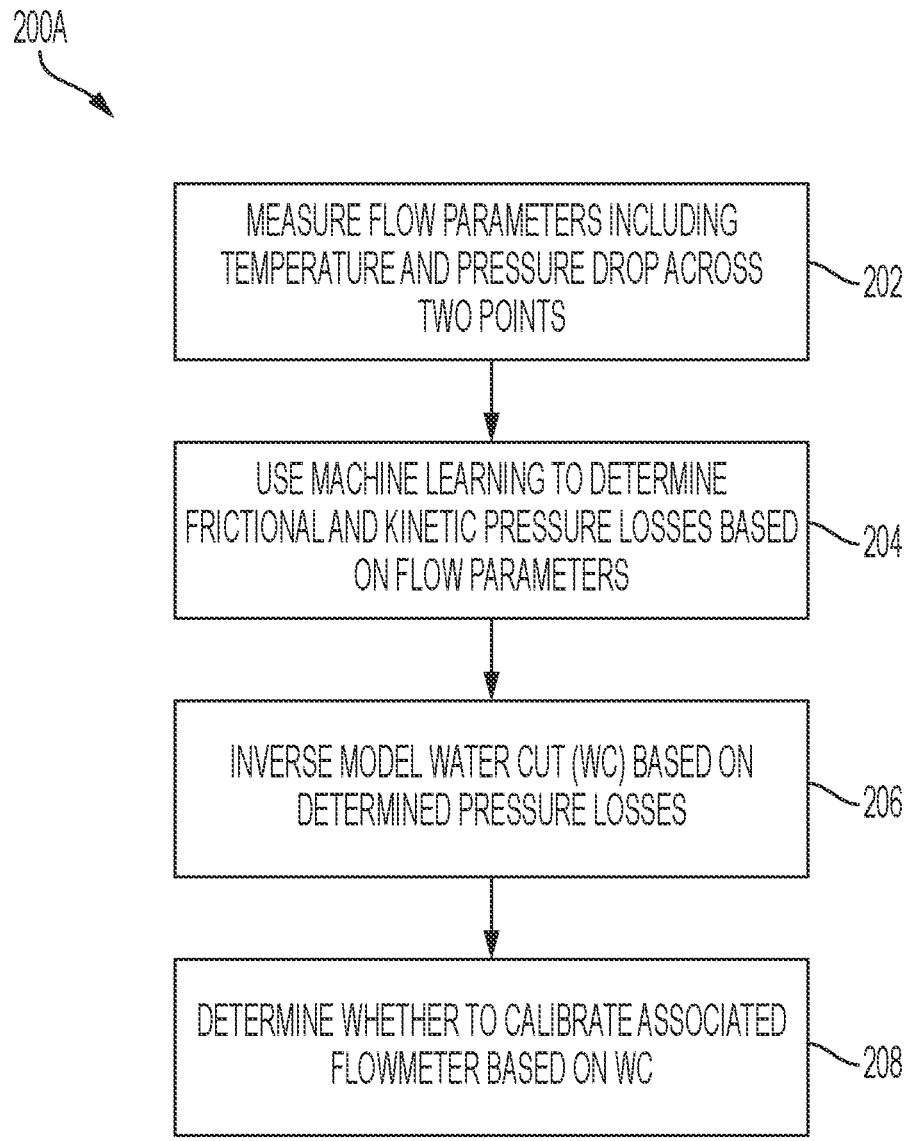
FIG. 2A illustrates a process for use of the intelligent water cut measurement solution of FIG. 1, according to one or more embodiments shown and described herein.
Figure 2B:
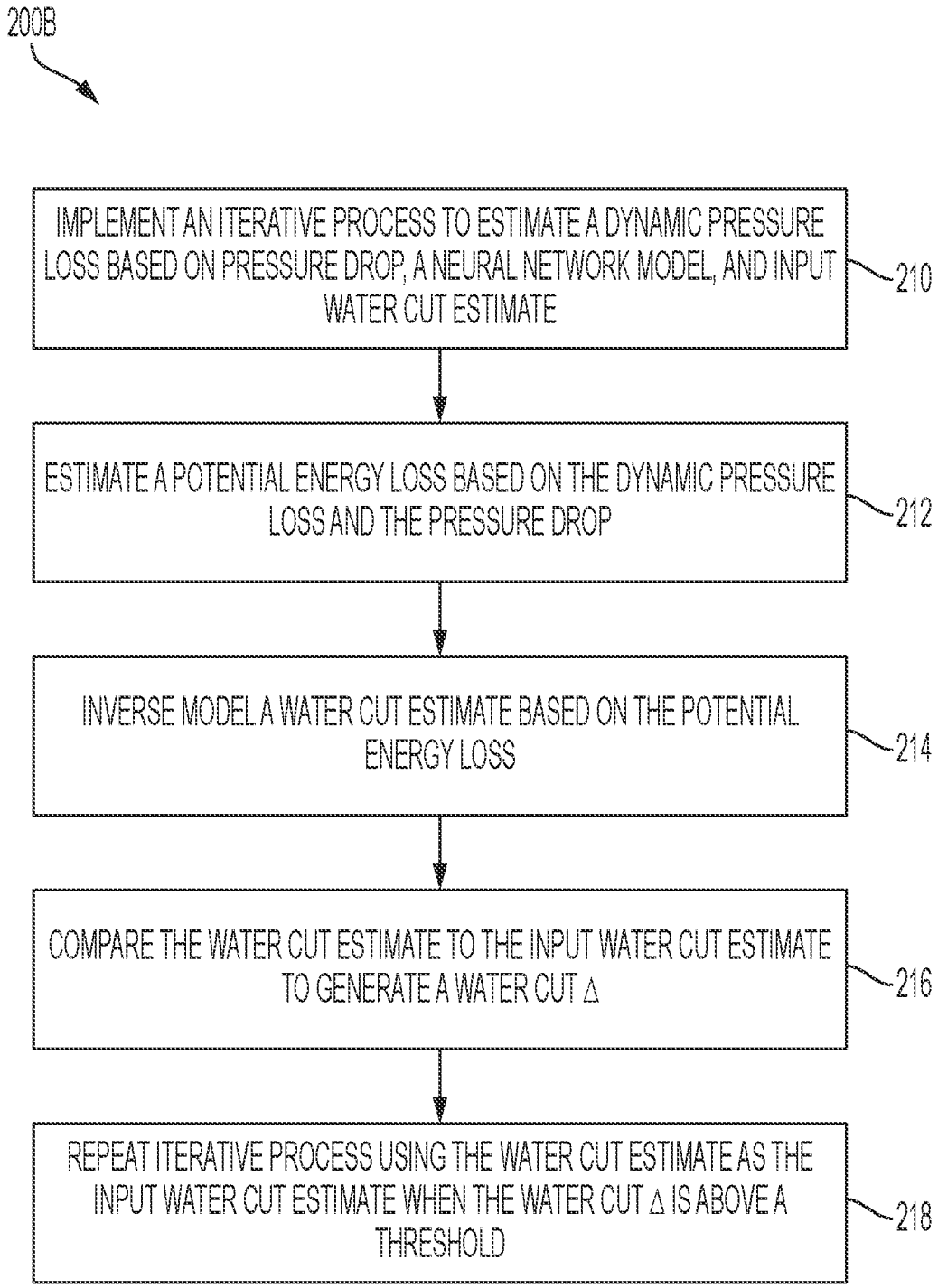
FIG. 2B illustrates another process for use of the intelligent water cut measurement solution of FIG. 1, according to one or more embodiments shown and described herein.

FIG. 2B depicts process 200B including blocks 210-214 associated with block 204 of process 200A and blocks 216-218 associated with block 206 of process 200A, as described in greater detail below. In block 204 of process 200A, machine learning is utilized to determine at least frictional and kinetic pressure losses based on the measured parameters of block 202 of process 200A. The data processor 304 may be operable to estimate a dynamic pressure loss based on the pressure drop, the one or more parameters of the neural network model, and the input water cut estimate to initiate an iterative process in block 210 of FIG. 2B, and estimate a potential energy loss based on the dynamic pressure loss and the pressure drop in block 212 of FIG. 2B. In general, the pressure drop across two points for incompressible fluids can be broken down to pressure losses due to potential energy, kinetic energy, and friction as per the following equation:

$$\Delta p = \Delta p_{PE} + \Delta p_{KE} + \Delta p_{PF} \quad \text{(EQUATION 1)}$$

In EQUATION 1, $\Delta p$ is representative of a pressure drop across two points for incompressible fluids, $\Delta p_{PE}$ is representative of pressure losses across the two points due to potential energy, $\Delta p_{KE}$ is representative of pressure losses across the two points due to kinetic energy, and $\Delta p_{PF}$ is representative of pressure losses across the two points due to friction. Incompressible fluids are fluids for which a density does not change when pressure changes. Incompressible fluids may reference fluids such as water for which a change of density due to changes in pressure associated with flow are very small and may be disregarded.

In many cases, pressure loss due to kinetic energy can be ignored because a pipe diameter between the two pressure sensors is often constant. On the other hand, frictional pressure loss is often significant and needs to be accounted for, especially when the distance between sensors is large. Frictional pressure losses are estimated from physical models or lab based correlations. However, this conventional approach may limit estimation accuracy because actual field conditions may differ from those used in ideal models or lab conditions for the estimations. In contrast, frictional pressure loss for the process 200A is estimated based on a data-driven machine learning approach as described herein. Significant parameters that correlate to frictional pressure losses and estimations are gross rate, pipe area, length in measured depth, water, and fluid properties. Other parameters that can also be indicative of water cut and are included in machine learning if available are ESP parameters, such as Volts, Amps, Horsepower, Speed, Motor Temperature, Discharge Temperature, and Number of Stages, and any other suitable ESP parameters as contemplated to one of ordinary skill in the art. In some cases when a distance between sensors is small and/or a pipe diameter is large, frictional effects may be negligible. Further, the pressure losses due to potential energy ($\Delta p_{PE}$) can be estimated via the following equation.

$$\Delta p_{PE} = (1-WC)g_O h_{TVD} + WC\, g_W h_{TVD} \quad \text{(EQUATION 2)}$$

In EQUATION 2, $g_O$ is representative of the oil pressure gradient, $g_W$ is representative of water pressure gradient, and $h_{TVD}$ is representative of the height of total vertical depth between two sensors.

In EQUATION 2, water cut (WC) may be a representative fraction that utilizes reliable WC measurements from a truth model. The pressure losses due to friction ($\Delta p_F$) and kinetic energy ($\Delta p_{KE}$), also referable to as dynamic energy losses ($\Delta p_{Dyn}$), may be calculated as follows:

$$\Delta p_{Dyn} = \Delta p_F + \Delta p_{KE} = p_{downstream} - p_{upstream} - \Delta p_{PE} \quad \text{(EQUATION 3)}$$

As set forth above, pressure losses due to kinetic energy is often negligible. A challenging part for calculating pressure drop across two points may thus be the calculation of frictional pressure losses and, if applicable, kinetic pressure losses. This present disclosure describes utilization of machine learning to determine such frictional and/or kinetic pressure losses. Once all pressure losses are reliably modeled, the water cut can be inverse modeled.

In block 206 of FIG. 2A, a water cut estimation is inverse modeled based on the determined frictional and kinetic pressure losses of block 204. Further referring to FIG. 2B, the data processor 304 may be operable to inverse model a water cut estimate based on the potential energy loss in block 214, compare the water cut estimate to the input water cut estimate to generate a water cut $\Delta$ in block 216, utilize the water cut estimate as the input water cut estimate for the iterative process when the water cut $\Delta$ exceeds a threshold, and continue the iterative process as set forth in block 218 until the water cut $\Delta$ is below the threshold. As a non-limiting example, machine learning may include multivariate nonlinear regression and Deep Learning and may be used to relate dynamic pressure losses to parameters such as gross rate, pressure at two sensors/gauges, temperature at the two sensors/gauges, distance between sensors/gauges in measured depth, pipe area, and fluid properties and, if applicable, volts, amps, horsepower, motor speed, motor temperature, discharge temperature, and number of Stages.

In an applied workflow, if a good match is obtained without including water cut, then the workflow moves to a Direct Approach of Step A. Otherwise, the workflow moves to an Iterative Approach of Step B in which the data processor 304 is operable to generate an input water cut estimate. In embodiments, the input water cut estimate may be generated based on at least the one or more parameters of the neural network model, the received temperature data, or combinations thereof. The one or more parameters of the neural network model may include gross rate, the received pressure data, received temperature data from at least temperature sensors disposed at each of the two points of the well bore, distance between the two points of the well bore, pipe area, fluid properties associated with the well bore, electrical properties associated with the well bore, or combinations thereof.

In Step A, using the machine learning algorithm to estimate the dynamic pressure losses, the workflow can estimate the potential energy as follows:

$$\Delta p_{PE} = p_{downstream} - p_{upstream} \Delta p_F - \Delta p_{KE} \quad \text{(EQUATION 4)}$$

The workflow can then estimate the water cut (WC) by re-arranging the following equation, ending Step A.

$$\Delta p_{PE} = (1-WC)g_O h_{TVD} + WC\, g_W h_{TVD} \quad \text{(EQUATION 5)}$$

In Step B, as Step B(1), the workflow starts with an initial guess of water cut ($WC_i$). In Step B(2), using the initial WC guess and the other known parameters, the machine learning algorithm is used to estimate the dynamic pressure losses. In step B(3), potential energy loss ($\Delta p_{PE}$) is estimated through application of EQUATION 4. In step B(4), the water cut (WC) is estimated by re-arranging EQUATION 5. In step B(5), if a difference between the estimated water cut (WC) and the initial guess of water cut ($WC_i$) is negligible, then Step B ends. For example, if $WC - WC_i < 0.001$, then Step B ends. Otherwise, the estimated water cut (WC) is utilized as the initial guess of water cut ($WC_i$) such that $WC = WC_i$ to repeat Step B starting from Step B(2).

In block 208, a determination of whether to calibrate the flowmeter 114 associated with the well bore 102 is made based on a comparison with the water cut estimation of block 206. By way of example, and not as a limitation, when the water cut estimation of block 206 is greater than a threshold value when compared to a value from the flowmeter 114, the process 200A results in a determination to calibrate the flowmeter 114. When the water cut estimation of block 206 is less than or equal to the threshold value when compared to the value from the flowmeter 114, the process 200A results in a determination to not calibrate the flowmeter 114. In embodiments, the intelligent water cut estimate system 300 may include the flowmeter 114 associated with the well bore 102 and configured to generate an estimated liquid gross rate of the well bore 102. The data processor 304 may be further operable to generate a flowmeter water cut value from the estimated liquid gross rate, compare the water cut estimate when the iterative process is ended to the flowmeter water cut value to determine a difference, determine whether the difference is greater than a flowmeter threshold, and calibrate the flowmeter 114 when the difference is greater than the flowmeter threshold.

In embodiments, to implement the process 200A, the following components and/or parameters are contemplated. Two real-time sensors, such as one in a bottom hole of the well bore 102 and one near or at the surface 104, may be used. The pressure should be above bubble point across the pressure measurement points. Further, sufficient amount of data points from real-time data should be obtained for more accurate machine learning results. Additionally, a sufficient amount of reliable WC measurements (e.g. separator testing, sampling, a well-calibrated meter) should be obtained for more accurate machine learning results as these points can be used as the truth model for data training of the machine learning module 316, described in greater detail below.

Utilizing the process 200A disclosed herein, it is possible to obtain continuous real-time water cut (WC) measurement despite a situation in which there is one flowmeter per drill site/platform, e.g., for multiple wells. This is possible because pressure/temperature sensors as described herein are very cost effective and readily available at the surface 104 and may be installed as part of wellhead sensors and at a bottom-hole area, such as installed as part of ESPs or a Permanent Down Hole Monitoring System (PDHMS).

Example 1

Figure 3:
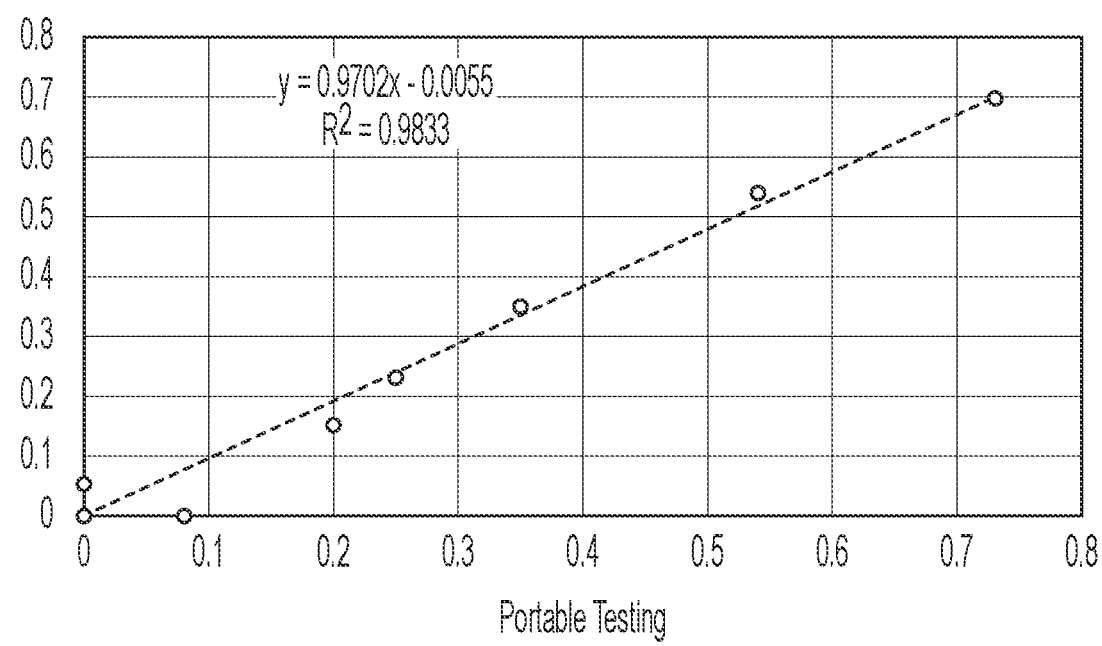
FIG. 3 illustrates a graphical depiction of results from an exemplary use of the process of FIG. 2A compared against portable testing, according to one or more embodiments shown and described herein.

Referring to FIG. 3, a graph 220 is depicted to display results from an exemplary use of the process 200A of FIG. 2A compared against a portable testing scheme as EXAMPLE 1. For experimentation and validation, the method of process 200A was conducted on field data with reservoirs of varying fluid properties, set forth herein as EXAMPLE 1. The method was calibrated and verified based on data confirmed with a wide range of measurements including separator testing, multi-phase flowmeters based on full-gamma spectroscopy, multi-phase flowmeters based on optical sensors, and sampling. Afterwards, the method was cross-validated with additional measurements in the year that followed. Validation results showed an excellent match with many of the measurements. Additionally, the results showed that flowmeters that were off from the estimated WC were due for calibration and that portable separator testing, sampling, confirmed the validity of the applied and tested method. The graph 220 illustrates the resulting estimations from the ESP calculations on the y-axis and portable separator testing results on the x-axis in a regression analysis, resulting in an equation of y−0.9702x−0.0055 with $R^2$=0.9833, almost at a linear fit of 1 and showing a near fit of the data to the fitted regression line. Thus, the results did not only validate the applied method but also demonstrated the applicability of the method to flag flowmeters that are due for calibration.

The EXAMPLE 1 experiment, with results as reflected in FIG. 3, was conducted in four different fields and six different reservoirs. The results of the graph 220 of FIG. 3 show excellent agreement between the method and the cross validation data, particularly with $R^2$=0.9833.

Figure 4:
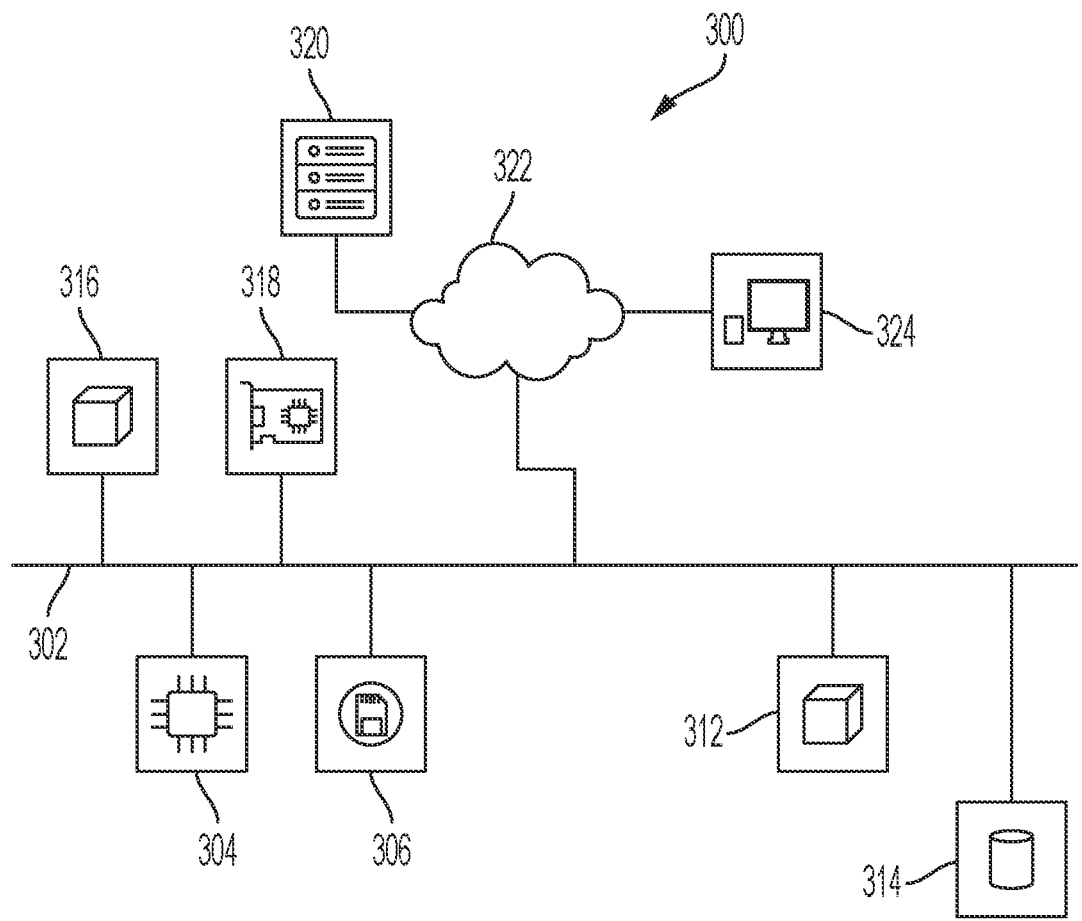
FIG. 4 illustrates a computer implemented system including an intelligent water cut measurement module and for use with the processes of FIGS. 2A-2B and the intelligent water cut measurement solution of FIG. 1, according to one or more embodiments shown and described herein.

FIG. 4 illustrates a computer implemented intelligent water cut measurement system 300 for use with the processes described herein, such as the processes 200A, 200B of FIGS. 2A-2B. Referring to FIG. 4, a non-transitory, intelligent water cut measurement system 300 for implementing a computer and software-based method, such as directed by the intelligent water cut measurement solution 100 and the process 200A, 200B described herein, to automatically generate an automated water cut estimation determination as described herein. The intelligent water cut measurement system 300 comprises an intelligent water cut measurement module 312 as a component of the data analytics module 112 of FIG. 1 to generate the automated water cut estimation determination.

The data analytics module 112 of FIG. 1 may be communicatively coupled to a "big data" environment including a database configured to store and process large volumes of data in such an environment. The database may be, for example, a structured query language (SQL) database or a like database that may be associated with a relational database management system (RDBMS) and/or an object-relational database management system (ORDBMS). The database may be any other large-scale storage and retrieval mechanism whether a SQL, SQL including, or a non-SQL database. For example, the database may utilize one or more big data storage computer architecture solutions. Such big data storage solutions may support large data sets in a hyperscale and/or distributed computing environment, which may, for example, include a variety of servers utilizing direct-attached storage (DAS). Such database environments may include Hadoop, NoSQL, and Cassandra that may be usable as analytics engines. Thus, while SQL may be referenced herein as an example database that is used with the tool described herein, it is understood that any other such type of database capable of support large amounts of database, whether currently available or yet-to-be developed, and as understood to those of ordinary skill in the art, may be utilized with the tool described herein as well.

The intelligent water cut measurement system 300 further comprises a communication path 302, one or more processors 304, a non-transitory memory component 306, the intelligent water cut measurement module 312, a storage or database 314, a machine learning module 316, a network interface hardware 318, a server 320, a network 322, and a computing device 324. The various components of the intelligent water cut measurement system 300 and the interaction thereof will be described in detail below.

While only one server 320 and one computing device 324 is illustrated, the intelligent water cut measurement system 300 can comprise multiple servers containing one or more applications and computing devices. In some embodiments, the intelligent water cut measurement system 300 is implemented using a wide area network (WAN) or network 322, such as an intranet or the internet. The computing device 324 may include digital systems and other devices permitting connection to and navigation of the network 322. It is contemplated and within the scope of this disclosure that the computing device 324 may be a personal computer, a laptop device, a smart mobile device such as a smartphone or smart pad, or the like. Other intelligent water cut measurement system 300 variations allowing for communication between various geographically diverse components are possible. The lines depicted in FIG. 4 indicate communication rather than physical connections between the various components.

The intelligent water cut measurement system 300 comprises the communication path 302. The communication path 302 may be formed from any medium that is capable of transmitting a signal such as, for example, conductive wires, conductive traces, optical waveguides, or the like, or from a combination of mediums capable of transmitting signals. The communication path 302 communicatively couples the various components of the intelligent water cut measurement system 300. As used herein, the term "communicatively coupled" means that coupled components are capable of exchanging data signals with one another such as, for example, electrical signals via conductive medium, electromagnetic signals via air, optical signals via optical waveguides, and the like.

The intelligent water cut measurement system 300 of FIG. 4 also comprises the processor 304. The processor 304 can be any device capable of executing machine readable instructions. Accordingly, the processor 304 may be a controller, an integrated circuit, a microchip, a computer, or any other computing device. The processor 304 is communicatively coupled to the other components of the intelligent water cut measurement system 300 by the communication path 302. Accordingly, the communication path 302 may communicatively couple any number of processors with one another, and allow the modules coupled to the communication path 302 to operate in a distributed computing environment. Specifically, each of the modules can operate as a node that may send and/or receive data.

The illustrated water cut measurement system 300 further comprises the memory component 306 which is coupled to the communication path 302 and communicatively coupled to the processor 304. The memory component 306 may be a non-transitory computer readable medium or non-transitory computer readable memory and may be configured as a nonvolatile computer readable medium. The memory component 306 may comprise RAM, ROM, flash memories, hard drives, or any device capable of storing machine readable instructions such that the machine readable instructions can be accessed and executed by the processor 304. The machine readable instructions may comprise logic or algorithm(s) written in any programming language such as, for example, machine language that may be directly executed by the processor, or assembly language, object-oriented programming (OOP), scripting languages, microcode, etc., that may be compiled or assembled into machine readable instructions and stored on the memory component 306. Alternatively, the machine readable instructions may be written in a hardware description language (HDL), such as logic implemented via either a field-programmable gate array (FPGA) configuration or an application-specific integrated circuit (ASIC), or their equivalents. Accordingly, the methods described herein may be implemented in any conventional computer programming language, as pre-programmed hardware elements, or as a combination of hardware and software components.

Still referring to FIG. 4, as noted above, the intelligent water cut measurement system 300 comprises the display such as a graphical user interface (GUI) on a screen of the computing device 324 for providing visual output such as, for example, information, graphical reports, messages, or a combination thereof. The display on the screen of the computing device 324 is coupled to the communication path 302 and communicatively coupled to the processor 304. Accordingly, the communication path 302 communicatively couples the display to other modules of the intelligent water cut measurement system 300. The display can comprise any medium capable of transmitting an optical output such as, for example, a cathode ray tube, light emitting diodes, a liquid crystal display, a plasma display, or the like. Additionally, it is noted that the display or the computing device 324 can comprise at least one of the processor 304 and the memory component 306. While the intelligent water cut measurement system 300 is illustrated as a single, integrated system in FIG. 4, in other embodiments, the systems can be independent systems.

The intelligent water cut measurement system 300 comprises the intelligent water cut measurement module 312 as described above, to at least apply data analytics and artificial intelligence algorithms and models to receive input data, and the machine learning module 316 for providing such artificial intelligence algorithms and models. The machine learning module 316 may include an artificial intelligence component to train and provide machine learning capabilities to a neural network as described herein. By way of example, and not as a limitation, a convolutional neural network (CNN) may be utilized. The intelligent water cut measurement module 312 and the machine learning module 316 are coupled to the communication path 302 and communicatively coupled to the processor 304. As will be described in further detail below, the processor 304 may process the input signals received from the system modules and/or extract information from such signals.

Data stored and manipulated in the intelligent water cut measurement system 300 as described herein is utilized by the machine learning module 316, which is able to leverage a cloud computing-based network configuration such as the cloud to apply Machine Learning and Artificial Intelligence. This machine learning application may create models that can be applied by the intelligent water cut measurement system 300, to make it more efficient and intelligent in execution. As an example and not a limitation, the machine learning module 316 may include artificial intelligence components selected from the group consisting of an artificial intelligence engine, Bayesian inference engine, and a decision-making engine, and may have an adaptive learning engine further comprising a deep neural network learning engine.

The intelligent water cut measurement system 200 comprises the network interface hardware 318 for communicatively coupling the intelligent water cut estimation system 300 with a computer network such as network 322. The network interface hardware 318 is coupled to the communication path 302 such that the communication path 302 communicatively couples the network interface hardware 318 to other modules of the intelligent water cut measurement system 300. The network interface hardware 318 can be any device capable of transmitting and/or receiving data via a wireless network. Accordingly, the network interface hardware 318 can comprise a communication transceiver for sending and/or receiving data according to any wireless communication standard. For example, the network interface hardware 318 can comprise a chipset (e.g., antenna, processors, machine readable instructions, etc.) to communicate over wired and/or wireless computer networks such as, for example, wireless fidelity (Wi-Fi), WiMax, Bluetooth, IrDA, Wireless USB, Z-Wave, ZigBee, or the like.

Still referring to FIG. 4, data from various applications running on computing device 324 can be provided from the computing device 324 to the intelligent water cut measurement system 300 via the network interface hardware 318. The computing device 324 can be any device having hardware (e.g., chipsets, processors, memory, etc.) for communicatively coupling with the network interface hardware 318 and a network 322. Specifically, the computing device 324 can comprise an input device having an antenna for communicating over one or more of the wireless computer networks described above.

The network 322 can comprise any wired and/or wireless network such as, for example, wide area networks, metropolitan area networks, the internet, an intranet, satellite networks, or the like. Accordingly, the network 322 can be utilized as a wireless access point by the computing device 324 to access one or more servers (e.g., a server 320). The server 320 and any additional servers generally comprise processors, memory, and chipset for delivering resources via the network 322. Resources can include providing, for example, processing, storage, software, and information from the server 320 to the intelligent water cut measurement system 300 via the network 322. Additionally, it is noted that the server 320 and any additional servers can share resources with one another over the network 322 such as, for example, via the wired portion of the network, the wireless portion of the network, or combinations thereof.

In an embodiment, the intelligent water cut measurement system 300 may include machine readable instructions stored in the memory component 306 communicatively coupled to the processor 204 to implement a control scheme such as the processes 200A, 200B of FIGS. 2A-2B.

Rather than relying on the use of analytical based models or lab based correlations to estimate water cut (WC), which may result in a poor match due to many assumptions incorporated in the analytical models and lab correlations, the present systems and methods use field data and machine learning methods to arrive at the WC estimations as described herein. Furthermore, because the machine learning approach described herein provides greater estimation accuracy, new and improved analytics and advisories become feasible such as the calibration advisory as described herein. Thus, the systems and methods as described herein provide a feasible solution for continuous water cut measurements without being limited in application to direct ESP-based measurements and without utilizing a numerous amount of assumptions as may be adapted for direct mathematical, analytical based models or lab based correlations.

The system and method embodiments of the present disclosure aid to provide a continuous water cut (WC) estimate at a wellhead in real-time, benchmark multi-phase flowmeters, instantly identify malfunctioning flowmeters, optimize flowmeter calibration frequencies and scheduling, interpolate between the often-sparse WC measurements, automatically determine production allocation per well in real-time, and/or can be implemented in many fields utilizing pressure and temperature sensors and an estimated liquid gross rate. Indeed, the system and method embodiments of the present disclosure may be used to flag meters that are due for calibration, which may enhance the measurement quality of existing meters while also optimizing cost via optimizing calibration frequency from a static periodically scheduled calibration to a more dynamic, as-needed-basis calibration based on the real-time flagging described herein.

The intelligent water cut measurement solution systems and methods as described herein assist to significantly reduce inefficiencies associated with well water cut estimation to result in faster and cost-effective water cut measurement estimation, for example. The present disclosure provides systems, methods, and computer programs for estimating water cut of one or more wells in real-time from indirect measurements such as temperature and pressure from one or more sensors as described herein without requiring on-site physical calibration of a flowmeter for the estimation but rather through utilizing a data-driven approach to estimate water cut as described herein. The intelligent water cut measurement solution systems and methods thus provide a more efficient processing system to efficiently and automatically handle water cut measurement estimation determinations in real-time, effectively reducing a use of processing power while optimizing system usage and efficiencies, while shortening the time to produce related water cut measurement estimation determinations.

For the purposes of describing and defining the present disclosure, it is noted that reference herein to a variable being a "function" of a parameter or another variable is not intended to denote that the variable is exclusively a function of the listed parameter or variable. Rather, reference herein to a variable that is a "function" of a listed parameter is intended to be open ended such that the variable may be a function of a single parameter or a plurality of parameters.

It is also noted that recitations herein of "at least one" component, element, etc., should not be used to create an inference that the alternative use of the articles "a" or "an" should be limited to a single component, element, etc.

It is noted that recitations herein of a component of the present disclosure being "configured" or "programmed" in a particular way, to embody a particular property, or to function in a particular manner, are structural recitations, as opposed to recitations of intended use.

It is noted that terms like "preferably," "commonly," and "typically," when utilized herein, are not utilized to limit the scope of the claimed disclosure or to imply that certain features are critical, essential, or even important to the structure or function of the claimed disclosure. Rather, these terms are merely intended to identify particular aspects of an embodiment of the present disclosure or to emphasize alternative or additional features that may or may not be utilized in a particular embodiment of the present disclosure.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present disclosure, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. An intelligent water cut estimation system comprising at least two pressure sensors, a neural network model, and a data processor, wherein:
    the at least two pressure sensors are configured to generate pressure data respectively associated with two points of a well bore;

the neural network model comprises one or more parameters indicative of water cut associated with a well bore; and the data processor is communicatively coupled to the at least two pressure sensors and the neural network model and is operable to:

receive pressure data from the at least two pressure sensors respectively indicative of the pressure at each of the two points of the well bore, determine a pressure drop between the two points based on the received pressure data from the at least two pressure sensors, generate an input water cut estimate, estimate a dynamic pressure loss based on the pressure drop, the one or more parameters of the neural network model, and the input water cut estimate to initiate an iterative process, estimate a potential energy loss based on the dynamic pressure loss and the pressure drop, inverse model a water cut estimate based on the potential energy loss, compare the water cut estimate to the input water cut estimate to generate a water cut $\Delta$, utilize the water cut estimate as the input water cut estimate for the iterative process when the water cut $\Delta$ exceeds a threshold, and continue the iterative process until the water cut $\Delta$ is below the threshold.

2. The intelligent water cut estimation system of claim 1 further comprising at least two temperature sensors, wherein the at least two temperature sensors are configured to generate temperature data respectively associated with the two points of the well bore.

3. The intelligent water cut estimation system of claim 2, wherein the one or more parameters of the neural network model comprise temperature data from the at least two temperature sensors.

4. The intelligent water cut estimation system of claim 1, wherein the input water cut estimate is based on at least the one or more parameters of the neural network model.

5. The intelligent water cut estimation system of claim 4, wherein the one or more parameters of the neural network model comprises gross rate, the received pressure data, received temperature data from at least temperature sensors disposed at each of the two points of the well bore, distance between the two points of the well bore, pipe area, fluid properties associated with the well bore, electrical properties associated with the well bore, or combinations thereof.

6. The intelligent water cut estimation system of claim 1, further comprising a flowmeter associated with the well bore and configured to generate an estimated liquid gross rate of the well bore.

7. The intelligent water cut estimation system of claim 6, wherein the data processor is further operable to generate a flowmeter water cut value from the estimated liquid gross rate, compare the water cut estimate when the iterative process is ended to the flowmeter water cut value to determine a difference, determine whether the difference is greater than a flowmeter threshold, and calibrate the flowmeter when the difference is greater than the flowmeter threshold.

8. An intelligent water cut estimation system comprising at least two pressure sensors, at least two temperature sensors, a neural network model, and a data processor, wherein:

the at least two pressure sensors are configured to generate pressure data respectively associated with two points of a well bore;

the at least two temperature sensors are configured to generate temperature data respectively associated with two points of a well bore;

the neural network model comprises one or more parameters indicative of water cut associated with a well bore; and the data processor is communicatively coupled to the at least two pressure sensors and the neural network model and is operable to:

receive pressure data from the at least two pressure sensors respectively indicative of the pressure at each of the two points of the well bore, receive temperature data from the at least two temperature sensors respectively indicative of the temperature at each of the two points of the well bore, determine a pressure drop between the two points based on the received pressure data from the at least two pressure sensors, generate an input water cut estimate based on at least the one or more parameters of the neural network model and the received temperature data, estimate a dynamic pressure loss based on the pressure drop, the one or more parameters of the neural network model, and the input water cut estimate to initiate an iterative process, estimate a potential energy loss based on the dynamic pressure loss and the pressure drop, inverse model a water cut estimate based on the potential energy loss, compare the water cut estimate to the input water cut estimate to generate a water cut $\Delta$, utilize the water cut estimate as the input water cut estimate for the iterative process when the water cut $\Delta$ exceeds a threshold, and continue the iterative process until the water cut $\Delta$ is below the threshold.

9. The intelligent water cut estimation system of claim 8, wherein the one or more parameters of the neural network model comprises gross rate, the received pressure data, the received temperature data, distance between the two points of the well bore, pipe area, fluid properties associated with the well bore, electrical properties associated with the well bore, or combinations thereof.

10. The intelligent water cut estimation system of claim 8, further comprising a flowmeter associated with the well bore and configured to generate an estimated liquid gross rate of the well bore.

11. The intelligent water cut estimation system of claim 10, wherein the data processor is further operable to generate a flowmeter water cut value from the estimated liquid gross rate, compare the water cut estimate when the iterative process is ended to the flowmeter water cut value to determine a difference, determine whether the difference is greater than a flowmeter threshold, and calibrate the flowmeter when the difference is greater than the flowmeter threshold.

12. An intelligent water cut estimation method comprising:

generating pressure data from at least two pressure sensors respectively associated with two points of a well bore;

storing one or more parameters indicative of water cut associated with a well bore in a neural network model;

receiving pressure data, by a data processor, from at least the two pressure sensors respectively indicative of the pressure at two points of the well bore;

determining a pressure drop between the two points based on the received pressure data from the at least two pressure sensors;

generating an input water cut estimate;

estimating a dynamic pressure loss based on the pressure drop, the one or more parameters of a neural network model, and the input water cut estimate to initiate an iterative process;

estimating a potential energy loss based on the dynamic pressure loss and the pressure drop;

inverse modeling a water cut estimate based on the potential energy loss;

comparing the water cut estimate to the input water cut estimate to generate a water cut Δ;

utilizing the water cut estimate as the input water cut estimate for the iterative process when the water cut Δ exceeds a threshold; and continuing the iterative process until the water cut Δ is below the threshold.

13. The intelligent water cut estimation method of claim 12, further comprising generating temperature data from at least two temperature sensors respectively associated with the two points of the well bore.

14. The intelligent water cut estimation method of claim 13, wherein the one or more parameters of the neural network model comprise temperature data from the at least two temperature sensors.

15. The intelligent water cut estimation method of claim 12, wherein the input water cut estimate is based on at least the one or more parameters of the neural network model.

16. The intelligent water cut estimation method of claim 15, wherein the one or more parameters of the neural network model comprises gross rate, the received pressure data, received temperature data from at least temperature sensors disposed at each of the two points of the well bore, distance between the two points of the well bore, pipe area, fluid properties associated with the well bore, electrical properties associated with the well bore, or combinations thereof.

17. The intelligent water cut estimation method of claim 12, further comprising a flowmeter associated with the well bore and configured to generate an estimated liquid gross rate of the well bore.

18. The intelligent water cut estimation method of claim 17, further comprising:

generating a flowmeter water cut value from the estimated liquid gross rate;

comparing the water cut estimate when the iterative process is ended to the flowmeter water cut value to determine a difference;

determining whether the difference is greater than a flowmeter threshold; and calibrating the flowmeter when the difference is greater than the flowmeter threshold.

* * * * *